US006437162B1

(12) United States Patent
O'Lenick, Jr.

(10) Patent No.: US 6,437,162 B1
(45) Date of Patent: Aug. 20, 2002

(54) PROCESS FOR THE MANUFACTURE OF LOW ODOR DIMETHICONE COPOLYOL COMPOUNDS

(75) Inventor: Anthony J. O'Lenick, Jr., Dacula, GA (US)

(73) Assignee: Siltech LLC, Dacula, GA (US)

( * ) Notice: Subject to any disclaimer, the term of this patent is extended or adjusted under 35 U.S.C. 154(b) by 0 days.

(21) Appl. No.: 09/910,357

(22) Filed: Jul. 23, 2001

(51) Int. Cl.[7] .................................................. C07F 7/08
(52) U.S. Cl. ........................................ 556/445; 556/449
(58) Field of Search .................................. 556/445, 449

(56) References Cited

U.S. PATENT DOCUMENTS 5,446,114 A * 8/1995 O'Lenick, Jr. .......... 556/445 X

* cited by examiner

Primary Examiner—Paul F. Shaver

(57) ABSTRACT

The present invention relates to a process for the manufacture of dimethicone copolyol compounds, which are free of odor and consequently suitable for use in personal care products. The process is one in which water is added to the dimethicone copolyol being treated, hydrolyzing susceptible groups off the compound and azeotropically distilling off the odor bodies.

10 Claims, No Drawings

PROCESS FOR THE MANUFACTURE OF LOW ODOR DIMETHICONE COPOLYOL COMPOUNDS

FIELD OF THE INVENTION

The present invention relates to a process for the manufacture of dimethicone copolyol compounds, which are free of odor and consequently suitable for use in personal care products. The process is one in which water is added to the dimethicone copolyol being treated, hydrolyzing susceptible groups off the compound and azeotropically distilling off the odor bodies.

BACKGROUND OF THE INVENTION

Certain types of non-hydrolyzable siloxane-polyether copolymers are well known in the art and are readily available through many suppliers. These materials are called dimethicone copolyol compounds. These compounds are manufactured by the co-reaction of poly(dimethylsiloxanes) containing SiH groups (hydrosiloxanes) with olefinic polyethers wherein the olefinic sites are allyl groups. The general reaction whereby these non-hydrolyzable linkages are created between silicone and polyether groups is:

groups break down giving odor. This latent odor source causes problems with odor stability over time.

Another source of concern is the HCl that is liberated when using hexachloroplatinic acid. It was clearly demonstrated by a group of French investigators that the hexachloroplatinic acid will liberate HCl as a by-product in the reaction system. This by-product is suspected to have a deleterious effect on the reaction system (for example, by inducing parallel protodesilylation reaction at the —C—Si— main chain bonds). This is shown by G. deMarignan, D. Teysse, S. Boileau, J. Malthete and C. Noel, Polymer, 29, 1318 (1988).

Several approached have been taken to reduce the presence of odor bodies in the dimethicone copolyol. U.S. Pat. No. 5,869,727 to Crane et al issued February 1999, incorporated herein by reference, attempts to remove the odor by running the hydrosilylation under a vacuum of 1–750 mmHg. This approach provides only minimal relief in that it does not address the hydrolysis of the competing Si—OR compounds addressed above, and does not take advantage of azeotropic distillation as a vehicle to remove the odor bodies.

Another approach has been used in U.S. Pat. No. 6,162,888 to Lee et all, incorporated herein by reference. The Lee

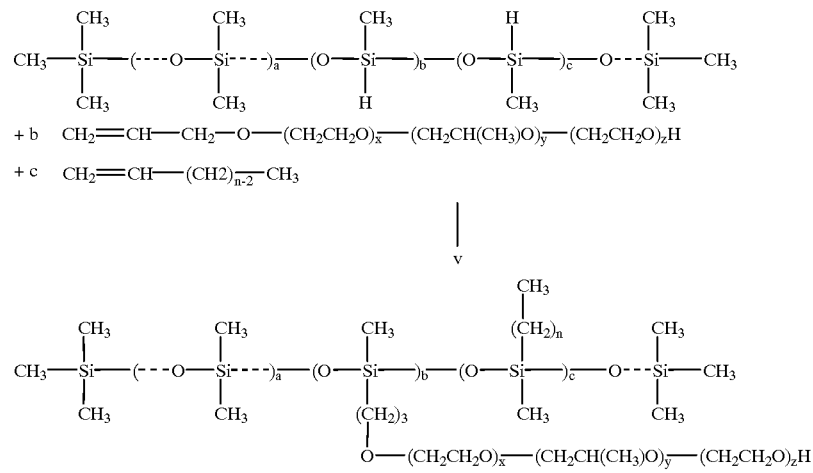

However, the above reaction is not the sole reaction that is taking place during the preparation of the copolymer. It has been established that a significant percentage of the allyl groups are isomerized under the addition reaction conditions to give propenyl polyethers, which do not participate in the hydrosilation reaction. See, for example, U.S. Pat. No. 5,869,727 to Crane et al issued February 1999.

It has become common practice in the industry to use stoichiometric excesses (20 mole % or more) of the allyl polyethers to insure reaction of all the SiH groups. The excess unreacted allyl polyether or isomerized propenyl polyether are thus present as inert diluents, thereby reducing the potency or active concentration of the final copolymer.

Another competing undesirable reaction is that some of the SiH groups react with sources of hydroxy containing contaminants, or solvents containing hydroxy functionality such as water, methanol or ethanol. These convert the SiH sites to SiOR sites acts to reduce the number of incorporated polyether moieties and it is known that the hydrogen gas released from this undesirable side reaction can be catalytically added across the double bond of the polyether. These invention relates to a method of making a silicone polyether comprising (I) reacting a mixture comprising an olefin functional polyether, an organohydrogensiloxane, and a homogeneous transition metal hydrosilylation catalyst, and (II) subjecting the product of (I) to hydrogen gas. The method of this invention reduces the amount of olefinic species present, which are precursors to odorous compounds. This approach has several drawbacks. While the hydrogenation does lower the amount of vinyl groups present, the resulting saturated compound has very little difference in boiling point and is not an improvement in odor.

| $CH_2$=CH—$CH_2OH$ | ----▶ | $CH_3$—$(CH_2)_2$—OH |
|---|---|---|
| Allyl Alcohol | | n-propanol |
| Boiling point 96–97° C. | | Boiling point 97° C. |

A third approach covered in U.S. Pat. No. 5,696,192 to Harashima deals with conducting a hydrosilylation reaction in an organic solvent between (A) a polyoxyalkylene bearing alkenyl at a single terminal and having a peroxide value not exceeding 3 meq/kg, and a total content of aldehyde plus ketone not exceeding 100 ppm by weight; (B) an organohydrogenpolysiloxane that contains at least one silicon-bonded hydrogen atom in the molecule; in the presence of (C) a platinum catalyst. A water treatment is then given but the amount of water is equivalent to at least one weight percent of the total amount of components (A) and (B); and the water is removed under reduced pressure.

We have surprisingly found that the incorporation of between 5 and 10% water followed by a boiling of the water at atmospheric conditions, up to a temperature of between 110 and 150 effectively controls the odor without the need for controlling the ketone level,, or the other steps outlined by Harashima. It has been surprisingly been found that the removal of water at atmospheric conditions, not under vacuum, and at elevated temperatures, rather than reduced temperatures facilitates the azeotropic distillation of the odor bodies from the dimethicone copolyol.

SUMMARY OF THE INVENTION

The present invention provides a simple effective and non-destructive method to eliminate the odor that is undesirable in the dimethicone copolyol compounds produced by the hydrosilation reaction. We have surprisingly found a process that effectively removes odor when applied to dimethicone copolyol compounds that have been prepared by hydrosilylation reactions known in the art. The process to deodorize dimethicone copolyol compounds relies upon the ability of water to hydrolyse odor-releasing compounds (principally Si—OR compounds) and to remove the volatile odor causing materials present in the dimethicone copolyol when the water is distilled off as the dimethicone copolyol is heated to between 110° and 150° C.

DETAILED DESCRIPTION OF THE INVENTION

The present invention makes use of the heretofore unappreciated facts that (1) water added to the finished dimethicone copolyol and allowed to mix for a period of time hydrolyses the Si—OR compounds that are made as a consequence of the hydrosilylation reaction, liberating all at once the odorous compounds that are removed in with water by distillation, (2) that only when elevated temperature is used to boil off the water and odorous materials is the odor successfully removed. Removing water under lower temperatures and reduced pressure simple does not allow for the ability to distill off odorous materials.

The present invention therefore is a process to deodorize dimethicone copolyol compounds conforming to the following structure:

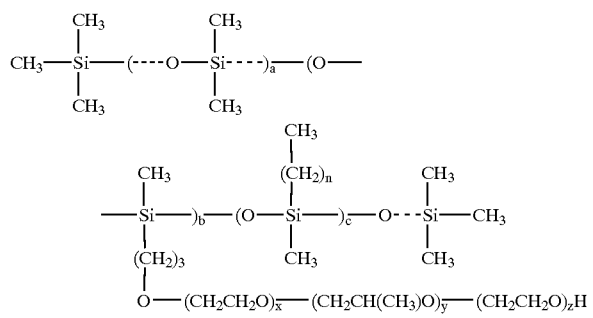

wherein;
a is an integer ranging from 0 to 2,000;
b is an integer ranging from 1 to 20;

c is an integer ranging from 0 to 20;
x, y and z are independently integers ranging from 0 to 20;
n is an integer ranging from 3 to 31;
which comprises;
  (a) add between 5 and 20 % by weight of water to said dimethicone copolyol;
  (b) mix the resulting mixture for between 10–30 minutes;
  (c) heat the reaction mixture to between 120° and 150° C. under atmospheric conditions;
  removing the distillate.

This procedure has been found to be very effective in providing products that are odor free for extended periods of time, and consequently f much interest to the personal care industry.

EXAMPLES

Dimethicone Copolyol Compounds

The dimethicone Copolyol compounds suitable for the practice of the present invention are commercially available from a variety of sources including Siltech Corporation of Toronto Ontario Canada.

All compounds presented here were analyzed by silicone-29 NMR and carbon-13 NMR. The structures were obtained from those analyses and are not dependant upon any trade names;

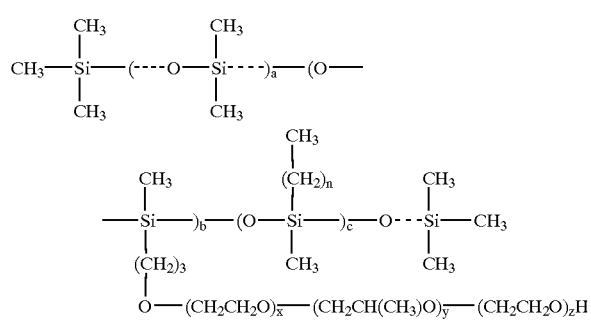

Preferred Embodiment

In a preferred embodiment a is an integer ranging from 1 to 20.

In a preferred embodiment b is an integer ranging from 0.

In a preferred embodiment b is an integer ranging from 1 to 5.

In a preferred embodiment x, y, and z range from 1 to 10.

In a preferred embodiment wherein b is 1–20.

In a preferred embodiment z is 0.

In a preferred embodiment z is 0 and x+y are between 8 and 15.

In a preferred embodiment z is 0 and x+y is 8.

In a preferred embodiment z is 0 and x+y is 12.

| Example | a | b | c | x | y | z | n |
|---------|-----|---|---|---|---|----|---|
| 1       | 10  | 4 | 0 | 8 | 0 | 0  | — |
| 2       | 20  | 5 | 0 | 1 | 5 | 12 | — |

-continued

| Example | a | b | c | x | y | z | n |
|---|---|---|---|---|---|---|---|
| 3 | 10 | 10 | 2 | 10 | 1 | 0 | 11 |
| 4 | 2 | 2 | 0 | 12 | 5 | 12 | 13 |
| 5 | 0 | 20 | 0 | 20 | 20 | 20 | — |
| 6 | 100 | 50 | 20 | 20 | 0 | 20 | 31 |

Process of this invention

To 1,000 grams of dimethicone copolyol add 100 grams of water, Mix well for 30 minutes, heat the reaction mixture to 130° C. under atmospheric conditions. The heating process will take about 1 hour. Hold at this temperature 1 hour. Distillate will begin to come off at 80° C. and continue throughout the strip.

Other Process (a) Vacuum removal of water

To 1,000 grams of dimethicone copolyol add 100 grams of water, apply vacuum and heat remove water.

(b) Atmospheric Strip no water

Heat 1,000 grams of dimethicone copolyol to 130° C. under atmospheric conditions, hold one hour.

Comparative Results

A panel of cosmetic formulators working with fragrances evaluated the products. The scale chosen ranged from 10 (no odor) to 1 (poor odor).

| Example | Process of this Invention | Alternative Process A | Alternative Process B | Untreated |
|---|---|---|---|---|
| 1 | 9 | 6 | 5 | 5 |
| 2 | 10 | 6 | 5 | 4 |
| 3 | 8 | 5 | 6 | 3 |
| 4 | 9 | 6 | 6 | 5 |
| 5 | 8 | 5 | 6 | 4 |
| 6 | 9 | 6 | 6 | 6 |

The data above shows that by using the process of the present invention, dimethicone copolyol compounds can be prepared that have more cosmetically acceptable odor. Consequently, these products that have enjoyed only minimal usage in personal care products, in large part due to the odor, can now be used more widely.

While the illustrative embodiments of the invention have been described with particularty, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claim be construed as encompassing all the features of patentable novelty which reside in the present invention, including all features which would be treated as equivalents thereof by those skilled in the art to which the invention pertains.

What is claimed:

1. A process to deodorize dimethicone copolyol compounds conforming to the following structure:

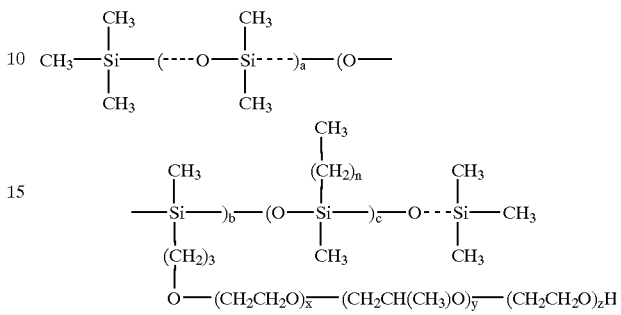

wherein;

a is an integer ranging from 0 to 2,000;

b is an integer ranging from 1 to 20;

c is an integer ranging from 0 to 20;

x, y and z are independently integers ranging from 0 to 20;

n is an integer ranging from 3 to 31;

which comprises;

(d) add between 5 and 20% by weight of water to said dimethicone copolyol;

(e) mix the resulting mixture for between 10–30 minutes;

(f) heat the reaction mixture to between 120° and 150° C. under atmospheric conditions;

removing the distillate.

2. A process of claim 1 wherein a is an integer ranging from 1 to 20.

3. A process of claim 1 wherein b is an integer ranging from 0.

4. A process of claim 1 wherein b is an integer ranging from 1 to 5.

5. A process of claim 1 wherein x, y, and z range from 1 to 10.

6. A process of claim 1 wherein b is 1–20.

7. A process of claim 1 wherein z is 0.

8. A process of claim 7 wherein x+y are between 8 and 15.

9. A process of claim 7 wherein x+y is 8.

10. A process of claim 7 wherein x+y is 12.

* * * * *